United States Patent [19]

Dolman et al.

[11] 4,396,617
[45] Aug. 2, 1983

[54] 2-ARYLAMINO-HEXAHYDROPYRIMI-DINES, COMPOSITIONS CONTAINING SAME, AND METHOD OF USE THEREOF

[75] Inventors: Hendrik Dolman; Johannes Kuipers, both of Weesp, Netherlands

[73] Assignee: Duphar International B.V., Netherlands

[21] Appl. No.: 264,461

[22] Filed: May 18, 1981

Related U.S. Application Data

[63] Continuation of Ser. No. 948,735, Oct. 5, 1978, abandoned.

[30] Foreign Application Priority Data

Oct. 18, 1977 [NL] Netherlands .................. 7711390

[51] Int. Cl.³ .................. A01N 43/54; A01N 239/14
[52] U.S. Cl. .................. 424/245; 424/251; 424/225; 424/226; 424/330; 424/331; 424/332
[58] Field of Search .............. 544/226, 330, 332, 225, 544/331; 424/251, 245

[56] References Cited

U.S. PATENT DOCUMENTS

| | | | |
|---|---|---|---|
| 2,899,426 | 8/1959 | Bloom | 544/330 |
| 2,899,434 | 8/1959 | Bloom | 544/330 |
| 3,202,660 | 8/1965 | Zeile et al. | 544/330 |
| 4,374,143 | 2/1983 | Dolman et al. | 424/251 |

*Primary Examiner*—Paul M. Coughlan, Jr.

*Attorney, Agent, or Firm*—Stevens, Davis, Miller and Mosher

[57] ABSTRACT

The invention relates to novel 2-aryliminohexahydropyrimidines and imidazolidines, of the formula

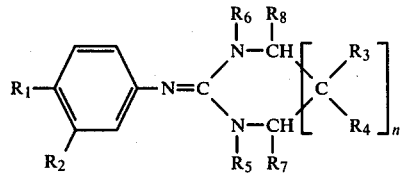

as well as to salts and complexes thereof, having fungicidal activity.

These compounds are particularly active against rust of beans, brown rust of wheat and mildew on cereals. After having been processed into compositions, the compounds of the invention can successfully be used to prevent or control mould infections in agriculture and horticulture in a dosage of 200–1000 g of active substance per hectare.

Very active fungicides are, for example, 2-(4-cyclohexyl-phenyl) iminohexahydropyrimidine and 2-(4-n-hexyl-phenyl) iminohexahydropyrimidine, as well as the sulphuric acid salts of these compounds and complexes with zinc salts.

55 Claims, No Drawings

2-ARYLAMINO-HEXAHYDROPYRIMIDINES, COMPOSITIONS CONTAINING SAME, AND METHOD OF USE THEREOF

This is a continuation of application Ser. No. 948,735, filed Oct. 5, 1978, now abandoned.

The invention relates to novel 2-arylimino-hexahydropyrimidines and -imidazolidines and to salts and complexes thereof. The invention also relates to a method of preparing the novel compounds, to fungicidal compositions which contain the novel compounds and to the use of said compositions in agriculture and horticulture to prevent and combat mould infections.

Imidazoline derivatives having a fungicidal activity are known from British Pat. No. 889,706. One compound described in said specification is 2-p-anilinophenylaminoimidazoline of the formula

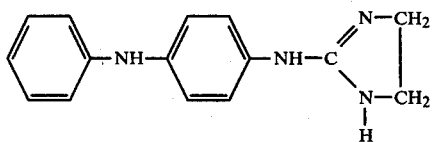

This compound is tautomeric with the corresponding iminoimidazolidine of the formula

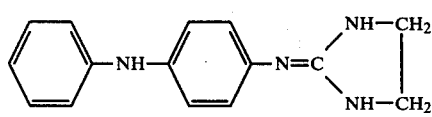

According to the present invention there are provided novel compounds of the general formula

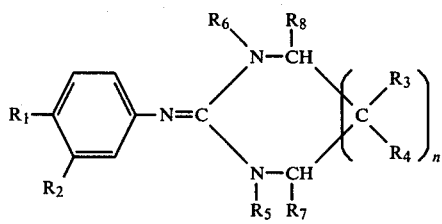

wherein n is 0 or 1, $R_1$ and $R_2$ are equal or different and represent hydrogen atoms, alkyl, alkyloxy or alkylthio groups having from 4 to 12 carbon atoms, cycloalkyl groups having from 3 to 7 carbon atoms, benzyloxy-, benzylthio-, phenoxy- or phenylthio groups optionally substituted with halogen or $C_1$–$C_4$ alkyl, phenylalkyl groups having from 7 to 11 carbon atoms, of which the phenyl group is optionally substituted with halogen, dialkylamino or with alkyl, alkoxy or alkylthio, which alkyl-, alkoxy- or alkylthio groups have from 1 to 6 carbon atoms and are optionally halogenated, furylalkyl- or thienylalkyl groups of which the alkyl groups have from 1 to 4 carbon atoms, dialkylamino groups the alkyl groups of which each have from 2 to 6 carbon atoms, or alkoxycarbonyl groups having from 4 to 12 carbon atoms, or wherein $R_1$ and $R_2$ together represent a trimethylene, tetramethylene or butadienylene group, with the proviso that $R_1$ and $R_2$ are not both hydrogen atoms, $R_3$, $R_4$, $R_7$ and $R_8$ are equal or different and represent hydrogen atoms or alkyl groups having from 1 to 4 carbon atoms, and $R_5$ and $R_6$ are equal or different and represent hydrogen atoms, alkyl groups having from 1 to 4 carbon atoms or alkanoyl groups having from 2 to 5 carbon atoms.

The present invention also includes novel salts and complexes of the aforesaid compounds.

The salts may be derived from mono- or multi-basic mineral or organic acids, such as sulphuric acid, nitric acid, phosphoric acid, carboxylic acids, phosphonic acids or sulphonic acids.

The complexes may be formed with salts of metals such as zinc, copper, nickel or cobalt.

The novel 2-arylimino-imidazolidines according to the invention, that is to say compounds of the above general formula wherein n=0, show a strong fungicidal activity and have proved to be very active notably against bean rust (*Uromyces phaseoli*). Among these imidazolidines the most interesting compounds are those in which $R_1$ is an alkyl or alkylthio group having from 4 to 12 carbon atoms, a cyclohexyl group, a phenylthio group optionally substituted with a halogen or $C_1$–$C_4$ alkyl, a phenyl alkyl group having 7 to 11 carbon atoms of which the phenyl group is optionally substituted with halogen, $C_1$–$C_6$ alkyl or $C_1$–$C_6$ alkoxy, a furylalkyl group of which the alkyl group has from 1 to 4 carbon atoms, or an alkoxy carbonyl group having from 4 to 12 carbon atoms, and $R_2$, $R_5$ and $R_6$ are hydrogen atoms.

Examples of 2-arylamino-imidazolidines according to the invention which can successfully be used as fungicides are:

(1) 2-(4-n-octylphenyl)imino-imidazolidine
(2) 2-(4-cyclohexylphenyl)imino-imidazolidine,
(3) 2-(4-n-hexylthiophenyl)imino-imidazolidine,
(4) 2-(4-n-butylthiophenyl)imino-imidazolidine,
(5) 2-[4-(4-methylphenylthio)phenyl]imino-imidazolidine,
(6) 2-[4-(4-chlorophenylthio)phenyl]-imino-imidazolidine,
(7) 2-(4-n-butylphenyl)imino-imidazolidine,
(8) 2-(4-n-hexylphenyl)imino-imidazolidine,
(9) 2-(4-n-heptylphenyl)imino-imidazolidine,
(10) 2-(4-n-octylthiophenyl)imino-imidazolidine,
(11) 2-(4-sec.octyloxycarbonylphenyl)imino-imidazolidine,
(12) 2-[4-(4-chlorophenylthio)phenyl]imino-4-methyl-imidazolidine.

The above-mentioned compounds have proven to be considerably more active as fungicides than the aforesaid known compound 2-p-anilinophenylaminoimidazoline as will appear from the following example. The results given in this example were obtained by determining the preventive activity against bean rust in the following manner.

Young dwarf French bean plants of approximately 10 cm high were sprayed with an aqueous suspension of the compounds to be tested in different concentrations. The plants thus treated were infected with *Uromyces phaseoli* by spraying the plants with an aqueous suspension containing per ml 300,000 spores of *Uromyces phaseoli*. After an incubation period of 10 days at a temperature of 18° C. and a relative humidity of 100%, it was determined to what extent the mould, if any, had developed.

In the example below the concentration of the compound used is indicated (in p.p.m.) and the protection against *Uromyces phaseoli* which was obtained with this concentration; 100% means total protection, 0% no protection at all.

| Compound | concentration (ppm) | protection % |
|---|---|---|
| 2-p-anilinophenyl amino imidazoline (known) | 10 | 60 |
| | 30 | 88 |
| | 100 | 88 |
| | 300 | 97 |
| 2-(4-cyclohexylphenyl)imino-imidazolidine | 10 | 100 |
| | 30 | 100 |
| 2-(4-n-hexylthiophenyl)imino imidazolidine | 10 | 97 |
| | 30 | 100 |
| | 100 | 100 |

The above table shows that the compounds according to the invention give full protection gainst *Uromyces phaseoli* even with a concentration of 10 and 30 ppm, respectively, whereas the known substance does not give full protection even in a concentration of 300 ppm.

Although the above described 2-arylamino-imidazolidines are effective fungicides, their fungicidal activity may be generally exceeded by the likewise new 2-arylimino-hexahydropyrimidines of the general formula

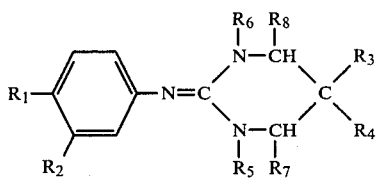

wherein $R_1$ and $R_2$ are equal or different and represent hydrogen atoms, alkyl, alkyloxy or alkylthio groups having from 4 to 12 carbon atoms, cycloalkylgroups having from 3 to 7 carbon atoms, benzyloxy, benzylthio-, phenoxy- or phenylthio groups optionally substituted with halogen or $C_1$-$C_4$ alkyl, phenylalkyl groups having from 7 to 11 carbon atoms, of which the phenyl group is optionally substituted with halogen, dialkylamino or with alkyl, alkoxy or alkylthio, which alkyl-, alkoxy- or alkylthio groups have from 1 to 6 carbon atoms and are optionally halogenated, furylalkyl- or thienylalkyl groups of which the alkyl groups have from 1 to 4 carbon atoms, dialkylamino groups of which the alkyl groups each have from 2 to 6 carbon atoms, or alkoxycarbonyl groups having from 4 to 12 carbon atoms, or wherein $R_1$ and $R_2$ together represent a trimethylene, tetramethylene or butadienylene group, with the proviso that $R_1$ and $R_2$ are not both hydrogen atoms, $R_3$, $R_4$, $R_7$ and $R_8$ are equal or different and represent hydrogen atoms or alkyl groups having from 1 to 4 carbon atoms, and $R_5$ and $R_6$ are equal or different and represent hydrogen atoms, alkyl groups having from 1 to 4 carbon atoms or alkanoyl groups having from 2 to 5 carbon atoms.

Salts and complexes of the above-described compounds are also very active and these compounds may be derived from acids such as sulphuric acid, nitric acid, phosphoric acid, phosphorous acid, phosphonic acids, carboxylic acids or sulphonic acids, of with salts of metals such as zink or copper.

Among these hexahydropyrimidines the most interesting compounds are those in which $R_1$ represents an alkyl or alkylthio group having from 4 to 12 carbon atoms, a cycloyexhyl group, a phenylthio group optionally substituted with a halogen or $C_1$-$C_4$ alkyl, a phenylalkyl group having from 7 to 11 carbon atoms of which the phenyl group is optionally substituted with halogen, $C_1$-$C_6$ alkyl or $C_1$-$C_6$ alkoxy, a furylalkyl group of which the alkyl group has from 1 to 4 carbon atoms, or an alkoxy carbonyl group having from 4 to 12 carbon atoms, and $R_2$, $R_3$, $R_4$, $R_5$ and $R_6$ are hydrogen atoms, as well as the salts and complexes derived therefrom.

Compounds of the hexahydropyrimidines according to the invention are very active not only against bean rust of beans but also act efficiently against brown wheat rust (*Puccinia recondita*), a mould against which hardly any or no protection has been possible up till now. This effectivity difference between the imidazolidines and the hexahydropyrimidines according to the invention is illustrated by the following example. The results stated were obtained by determining the protection against brown rust of wheat in the following manner:

Young wheat plants, approximately 10 cm high, were sprayed with an aqueous suspension of the compound to be tested in different concentrations. The plants thus treated were then infected with *Puccinia recondita* by spraying the plants with an aqueous suspension containing per ml 300,000 spores of *Puccinia recondita*. After an incubation period of 9 days at a temperature of 18° C. and a relative humidity of approximately 80% under continuous illumination, it was checked whether the mould had developed and, if so, to what extent.

In the example below the minimum concentration of the compound used is stated (in ppm), at which an effective protection of the relevant crop, in this case wheat, against *Puccinia recondita* was still found.

| Compound | min. concentration in ppm. |
|---|---|
| 2-(4-cyclohexylphenyl)imino-imidazolidine | >300 |
| 2-(4-cyclohexylphenyl)imino-hexahydropyrimidine | 100–300 |

Furthermore, these compounds also have an interesting activity against mildew on cereals (*Erysiphe graminis*); the preventive activity against attack by *Erysiphe graminis* was determined in the following manner:

Young barley plants, approximately 10 cm high, were sprayed with an aqueous suspension of the compound to be tested in different concentration. After drying up of the liquid, the barley plants were infected with spores of *Erysiphe graminis*. After an incubation period of 10 days at a temperature of 18° C. and a relative humidity of approximately 80% it was investigated to what extent the mould, if any, had developed.

In addition to a fungicidal activity with respect to the above-described pathogenic moulds, the compounds according to the invention also provide a good protection against *Puccinia striiformis* (on wheat), *Podosphaera leucotricha* (on apple), *Sphaerotheca fuliginea* (on cucumber), *Venturia inaqualis* (on apple), Septoria sp. (on sunflower), *Phytophthora infestans* (on tomato) and *Plasmopara viticola* (on grape).

The special effect of these compounds is in particular the activity of said compounds against pathogenic moulds which can occur simultaneously on the same crop and are combated by the same treatment. This applies, for example, with respect to *Erisiphe graminis*, *Puccinia recondita* and *Puccinia striiformis* on wheat and *Podosphaera leucotricha* and *Venturia inaequalis* on apple. In particular those pathogenic moulds which cause the known diseases, "mildew" and "rust" on cereals, are very sensitive to compounds according to the invention. For example, field tests have demonstrated that with 0.2–1.0 kg per hectare of the active substances 2-(4-cyclohexylphenyl)imino-hexahydropyrimidine and 2-(4-n-hexylphenyl)imino-hexahydropyrimidine, as well as of the salts and complexes of said compounds, there can be obtained a good protection of barley against attack by *Erisiphe graminis* and of wheat against attack by *Erysiphe graminis* and *Puccinia recondita* and *Puccinia striiformis*, respectively.

The curative effect of these compounds has also been proved. An infection of *Erisiphe graminis* and *Puccinia recondita* and *Puccinia triiformis*, respectively, already present in the crop could be stopped completely by a treatment with 0.4–0.8 kg of active substance per ha.

Examples of 2-arylimino-hexahydropyrimidines according to the invention which can successfully be used as fungicides are:

(13) 2-(4-n-butylphenyl)imino-hexahydropyrimidine,
(14) 2-(4-isobutylphenyl)imino-hexahydropyrimidine,
(15) 2-(4-hexylphenyl)imino-hexahydropyrimidine,
(16) 2-(4-cyclohexylphenyl)imino-hexahydropyrimidine,
(17) 2-(4-n-octylphenyl)imino-hexahydropyrimidine,
(18) 2-(4-n-decylphenyl)imino-hexahydropyrimidine,
(19) 2-(4-n-dodecyloxyphenyl)imino-hexahydropyrimidine,
(20) 2-(n-butylthiophenyl)imino-hexahydropyrimidine,
(21) 2-(3-n-hexylthiophenyl)imino-hexahydropyrimidine,
(22) 2-(4-n-hexylthiophenyl)imino-hexahydropyrimidine,
(23) 2-[4-(4-methylphenylthio)phenyl]imino-hexahydropyrimidine,
(24) 2-[4-(4-chlorophenylthio)phenyl]imino-hexahydropyrimidine,
(25) 2-(4-n-hexyloxycarbonylphenyl)imino-hexahydropyrimidine,
(26) 2-(4-n-octyloxycarbonylphenyl)imino-hexahydropyrimidine,
(27) 1-methyl-2-(4-cyclohexylphenyl)imino-hexahydropyrimidine,
(28) 2-(4-cyclohexylphenyl)imino-5,5-dimethylhexahydropyrimidine,
(29) 1,3-diacetyl-2-(4-cyclohexylphenyl)imino-hexahydropyrimidine,
(30) 2-(3,4-tetramethylenephenyl)imino-hexahydropyrimidine,
(31) 2-(4-n-pentylphenyl)imino-hexahydropyrimidine,
(32) 2-(4-sec.pentylphenyl)imino-hexahydropyrimidine,
(33) 2-(4-n-heptylphenyl)imino-hexahydropyrimidine,
(34) 2-(4-n-nonylphenyl)imino-hexahydropyrimidine,
(35) 2-(4-n-dodecylphenyl)imino-hexahydropyrimidine,
(36) 2-(4-benzylphenyl)imino-hexahydropyrimidine,
(37) 2-[4-(2-phenylethyl)phenyl]imino-hexahydropyrimidine,
(38) 2-(4-n-octylthiophenyl)imino-hexahydropyrimidine,
(39) 2-(4-n-hexyloxyphenyl)imino-hexahydropyrimidine,
(40) 2-(4-n-octyloxyphenyl)imino-hexahydropyrimidine,
(41) 2-(4-N,N,N-dibutylaminophenyl)imino-hexahydropyrimidine,
(42) 2-($\beta$naphthyl)imino-hexahydropyrimidine,
(43) 1-methyl-2-(4-n-butylphenyl)imino-hexahydropyrimidine,
(44) 1-methyl-2-(4-n-hexylphenyl)imino-hexahydropyrimidine,
(45) 2-[4-{2-(4-methylphenyl)ethyl}phenyl]imino-hexahydropyrimidine,
(46) 2-(4-cyclohexylphenyl)imino-4-methyl-hexahydropyrimidine,
(47) 2-(4-n-butylphenyl)imino-4-methyl-hexahydropyrimidine,
(48) 2-(4-n-octylphenyl)imino-4-methyl-hexahydropyrimidine,
(49) 2-[4-{2-(2-methylphenyl)ethyl}phenyl]imino-hexahydropyrimidine,
(50) 2-[4-{2-(4-isopropylphenyl)ethyl}phenyl]imino-hexahydropyrimidine,
(51) 2-[4-{2-(4-ethoxyphenyl)ethyl}phenyl]imino-hexahydropyrimidine,
(52) 2-[4-{2-(4-isopropoxyphenyl)ethyl}phenyl]imino-hexahydropyrimidine,
(53) 2-[4-{2-(4-chlorophenyl)ethyl}phenyl]imino-hexahydropyrimidine,
(54) 2-[4-{2-(2-chlorophenyl)ethyl}phenyl]imino-hexahydropyrimidine,
(55) 2-[4-{2-(3,4-dichlorophenyl)ethyl}phenyl]imino-hexahydropyrimidine,
(56) 2-[4-(2-furylethyl)phenyl]imino-hexahydropyrimidine,
(57) 2-(4-isopentylthiophenyl)imino-hexahydropyridine,
(58) 2-[4-{2-(4-n-butoxyphenyl)ethyl}phenyl]imino-hexahydropyrimidine, and
(59) 2-[4-{2-(4-benzylphenyl)ethyl}phenyl]imino-hexahydropyrimidine.

Examples of salts and complexes according to the invention effective as fungicides are:

(60) 2-(4-cyclohexylphenyl)imino-hexahydropyrimidine sulphate,
(61) 2-(4-cyclohexylphenyl)imino-hexahydropyrimidine cinnamate,
(62) 2-(4-cyclohexylphenyl)imino-hexahydropyrimidine $\beta$-chloroethane phosphonate,
(63) 2-(4-cyclohexylphenyl)imino-hexahydropyrimidine-p-dodecylbenzene sulphonate,
(64) 2-(4-cyclohexylphenyl)imino-hexahydropyrimidine acetate,
(65) 2-(4-n-octylphenyl)imino-hexahydropyrimidine acetate,
(66) 2-(4-cyclohexylphenyl)imino-hexahydropyrimidine phosphorous acid ethyl ester,
(67) 2-(4-cyclohexylphenyl)imino-hexahydropyrimidine-phosphorous acid-n-butylester,
(68) 2-(4-n-butylphenyl)imino-hexahydropyrimidine p-dodecylbenzene sulphonate,
(69) 2-(4-cyclohexylphenyl)imino-hexahydropyrimidine zinc chloride complex,
(70) 2-(4-cyclohexylphenyl)imino-hexahydropyrimidine zinc acetate complex,
(71) 2-(4-cyclohexylphenyl)imino-hexahydropyrimidine cupriacetate complex,

(72) 2-(4-n-octylphenyl)imino-hexahydropyrimidine zinc chloride complex, and
(73) 2-(4-n-butylphenyl)imino-hexahydropyrimidine cupriacetate complex.

For practical applications, the active substances according to the invention are formulated into compositions. In such compositions the active substance is mixed with a solid carrier material or dissolved or dispersed in a liquid carrier material, if desired in combination with auxiliary substances, such as emulsifiers, wetting agents, dispersing agents and stabilisers.

Examples of compositions according to the invention are aqueous solution and dispersions, oil solutions and oil dispersions, solutions in organic solvents, pastes, dusting powders, dispersible powders, miscible oils, granules, pellets, invert emulsions, aerosol compositions and smoke generating candles.

Dispersible powders, pastes and miscible oils are compositions in concentrated form which are diluted prior to or during use.

The invert emulsions and solutions in organic solvents are mainly used in air application, namely when large areas have to be treated with a comparatively small quantity of composition. The invert emulsion can be prepared shortly prior to or even during spraying in the spraying apparatus by emulsifying water in an oil solution or an oil dispersion of the active substance. The solutions of the active substances in organic solvents may be provided with a phytotoxicity-reducing substance, such as wool fat, wool fatty acid or wool fatty alcohol. A few forms of compositions will be described in detail below by way of example.

Granular compositions are prepared, for example, by taking up dispersing the active substance in a solvent thinner and impregnating the resulting solution suspension, if desired in the presence of a binder, on granular carrier material, such as porous granules (for example pumice and attaclay), mineral non-porous granules (sand or ground marl), organic granules for example dried coffee grounds, cut tobacco stems and corncob.

A granular composition can also be prepared by compressing the active substance together with powdered minerals in the presence of lubricants and binders and disintegrating and sieving the compressed product to the desired grain size.

Another possibility for preparing granules is by using the glomulation technique.

Dusting powders can be obtained by intimately mixing the active substance with an inert solid carrier material, for example talc.

Dispersible powders are prepared by mixing 10 to 80 parts by weight of the solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersion agent, for example, the lignin sulphonates or alkylnaphthalene sulphonates known for this purpose, and conveniently also 0.5 to 5 parts by weight of a wetting agent, for example fatty alcohol sulphates, alkylarylsulphonates, fatty acid condensation products, or polyoxyethylene compounds.

For the preparation of miscible oils, the active compound may be dissolved in a suitable solvent which preferably is poorly water-miscible and one or more emulsifiers are added to this solution. Suitable solvents are, for example, xylene, toluene, petroleum distillates which are rich in aromates, for example solvent naphta, distilled tar oil and mixtures of these liquids. As emulsifiers there may be used, for example, polyoxyethylene compounds and/or alkylarylsulphonates. The concentration of the active compound in said miscible oils is not restricted to narrow limits and may vary, for example, between 2 and 50% by weight. In addition to a miscible oil, a solution of the active substance in a readily water-miscible liquid, for example a glycol or glycolether, may be mentioned as a liquid and highly-concentrated primary composition, to which solution a dispersion agent and possibly a wetting agent have been added. When being diluted with water shortly prior to or during spraying, an aqueous dispersion of the active substance is obtained.

An aerosol composition according to the invention is obtained in the usual manner by incorporating the active substance, possibly in a solvent, in a volatile liquid to be used as a propellant gas, for example a mixture of chloro-fluoro derivatives of methane and ethane, a mixture of lower hydrocarbons, dimethylether, or gases likes $CO_2$, $N_2$ or $N_2O$.

Smoke generating candles or smoke generating powders, i.e. compositions which can develop a pesticidal smoke while burning, are obtained by taking up the active substance in a combustible mixture which may contain as a fuel, for example a sugar or a wood, preferably in the ground form, a substance to maintain combustion, for example ammonium nitrate or potassium chlorate, and furthermore a substance to delay combustion, for example kaolin, bentonite and/or colloidal silicic acid.

In addition to the above-mentioned ingredients, the agents according to the invention may also comprise other substances known for use in this kind of agents.

For example, a lubricating agent, such as calcium stearate or magnesium stearate, may be added to a dispersible powder or a mixture to be granulated. For example "adhesives", such as polyvinyl alcohol cellulose derivatives or other colloidal materials, such as casein, may also be added so as to improve the adhesion of pesticidal agent to the crop.

Known pesticidal compounds may also be incorporated in the compositions according to the invention. As a result of this the activity spectrum of the composition is widened and synergism may occur.

For use in such a combination composition the following known insecticidal, fungicidal and acaricidal compounds are to be considered.

Insecticides such as:
1. chlorinated hydrocarbons, for example, 2,2-bis(p-chlorophenyl)-1,1,1-trichloroethane and hexachloro-epoxyoctahydrodimenthanonaphthalene;
2. carbamates, for example N-methyl-1-naphthyl-carbamate;
3. dinitrophenols, for example 2-methyl-4,6-dinitrophenol and 2-(2-butyl)-4,6-dinitrophenyl 3,3-dimethyl-acrylate;
4. organic phosphorus compounds, for example dimethyl-2-methoxycarbonyl-1-methylvinyl-phosphate; O,O-diethyl-O-p-nitrophenylphosphorthioate; N-monomethylamide of O,O-dimethyldithiophosphoryl acetic acid;
5. benzoylurea derivatives, for example N-(2,6-difluorobenzoyl)-N'-(4-chlorophenyl)urea.

Acaricides, such as:
1. diphenylsulphides, for example p-chlorobenzyl p-chlorophenylsulphide and 2,4,4,5-tetrachlorodiphenyl sulphide;

2. diphenylsulphonates, for example p-chlorophenyl benzene sulphonate;
3. methylcarbinols, for example 4,4-dichloro-α-trichloromethylbenzhydrol;
4. quinoxaline compounds such as methylquinoxaline dithiocarbonate.

Fungicides, such as:
1. organic tin compounds, for example triphenyl tin hydroxide and triphenyl tin acetate;
2. alkylenebisdithiocarbamates, for example zinc-ethylenebisdithiocarbamate and manganese ethylenebisdithiocarbamate;
3. 1-acyl- or 1-carbamoyl-N-benzimidazole (-2) carbamates and 1,2-bis(3-alkoxycarbonyl)-2-thioureido)-benzene; and in addition 2,4-dinitro-6-(2-octylphenyl-crotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidine methanol, 1-(isopropyl-carbamoyl)-3-(3,5-dichlorophenyl)hydantoine, N-(1,1,2,2-tetrachloroethylthio)-4-cyclohexene-1,2-carboximide, N-trichloromethylmercapto-4-cyclo-hexane-1,2-dicarboximide, and N-tridecyl-2,6-dimethyl-morpholine.

The dosage desired for application of the composition according to the invention will depend inter alia on the active substance chosen, the form of composition, the type of crop which is to be protected against mould attack, the type of mould which is to be combated, the position of the crop and the wheather conditions.

In general it holds that favourable results are achieved with a dosage which corresponds from 200 to 1000 g of the active substance per ha.

The compounds according to the invention are novel substances, which can be prepared in a manner known per se for related compounds.

For example, the compounds according to the invention can be prepared by causing H₂S to be split off with ring closure from a compound of the general formula

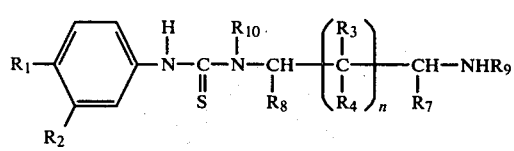

wherein n, $R_1$, $R_2$, $R_3$, $R_4$, $R_7$ and $R_8$ have the above meanings, and $R_9$ and $R_{10}$ are equal or different and represent hydrogen atoms or alkyl groups with from 1 to 4 carbon atoms, in which a product is obtained of the general formula

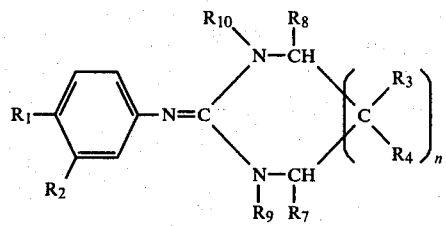

which if desired, when $R_9$ and $R_{10}$ represent hydrogen atoms, is reacted with a carboxylic acid halide or carboxylic acid anhydride, to give a product of the general formula

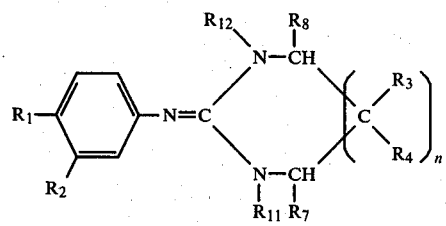

wherein $R_{11}$ and $R_{12}$ are alkanoyl groups having from 2 to 5 carbon atoms.

This ring closure reaction is carried out under the influence of a catalyst, preferably a heavy metal compound such as a mercury compound. Polar organic solvents are particularly suitable for this reaction such as, acetonitrile, methanol, ethanol, methoxy ethanol, and dimethoxy ethane, at a reaction temperature between 0° C. and the coiling point of the solvent used. The reaction may conveniently be carried out at room temperature or a slightly elevated temperature. During the reaction there is formed, in addition to the heavy metal sulphide, an acid which can be bound by means of a base. As such a base there may be used not only an inorganic base, for example sodium hydroxide, but also an organic base, for example, an amine such as triethylamine. If desired, the final product may be purified by recrystallisation. The purification may alternatively be carried out by converting the final product by means of an inorganic acid into a salt and dissolving said salt in water. Non-basic contaminations can then be washed away by means of a water-immiscible organic solvent, for example diethyl ether, after which the final product can be isolated again by means of an inorganic base.

In another embodiment the compounds can be prepared by reacting a compound of the general formula

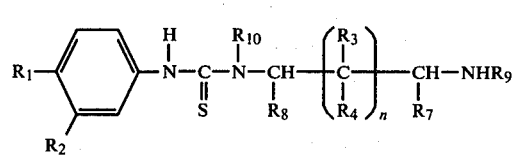

wherein n, $R_1$, $R_2$, $R_3$, $R_4$, $R_7$, $R_8$, $R_9$ and $R_{10}$ have the above meanings, with an alkylating agent, in which a product is formed of the general formula

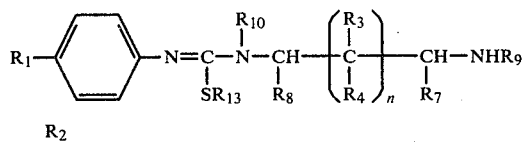

wherein $R_{13}$ represents an alkyl group having from 1 to 4 carbon atoms, after which $R_{13}SH$ is caused to split off with ring closure, to give a product of the general formula

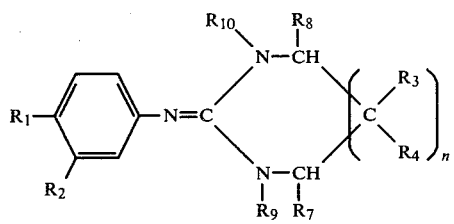

which, if desired, when $R_9$ and $R_{10}$ represent hydrogen atoms, is converted in the manner described above into a product of the general formula

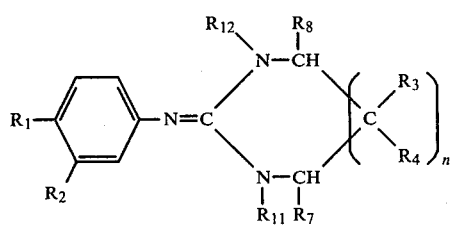

wherein $R_{11}$ and $R_{12}$ are alkanoyl groups having from 2 to 5 carbon atoms.

The alkylation and the ring closure reaction are usually carried out in one process step, without isolating the intermediate product, in a polar organic solvent, for example an alcohol, dimethyl formamide, a dialkoxy ethane or an alkoxy ethanol, preferably at elevated temperature, for example the boiling point of the solvent used. As an alkylating agent an alkyl halide or a dialkyl sulphate is used. In order to liberate the final product from the salt, a base may be used during or preferably after the reaction.

In a further embodiment for the preparation of the compounds of the invention a compound of the general formula

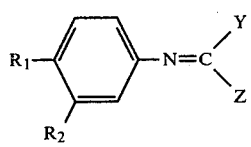

wherein $R_1$ and $R_2$ have the above meanings, and Y and Z both may be halogen atoms or alkylthio groups, or, when Y is an amino group, Z represents an alkoxy or alkylthio group is reacted with a compound of the general formula

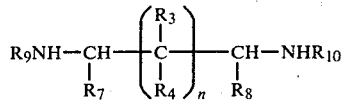

wherein n, $R_3$, $R_4$, $R_7$, $R_8$, $R_9$ and $R_{10}$ have the above meanings, in which, while splitting off HY and HZ a product is obtained of the general formula

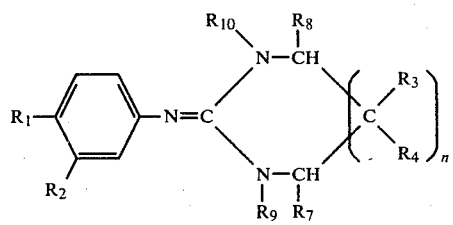

which, if desired, when $R_9$ and $R_{10}$ represent hydrogen atoms, is converted in the manner described above into a product of the general formula

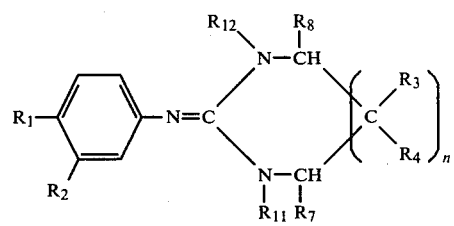

wherein $R_{11}$ and $R_{12}$ are alkanoyl groups having from 2 to 5 carbon atoms.

In addition to the diamine, the starting substance preferably chosen is an S-alkyl isothiourea derivative or a salt thereof, a dichloromethylene amine, or an iminodithiocarbonate. This reaction is carried out in the same reaction conditions as indicated in the above-described mode or preparation.

The compounds may also be synthesized by reacting a compound of the general formula

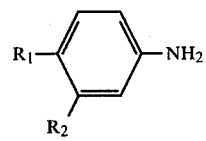

wherein $R_1$ and $R_2$ have the above indicated meanings, with a compound of the general formula

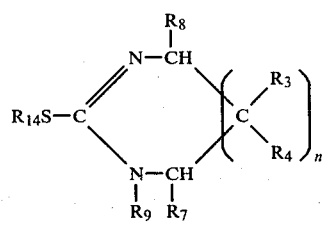

wherein n, $R_3$, $R_4$, $R_7$ and $R_8$ have the above indicated meanings, $R_9$ represents a hydrogen atom or an alkyl group having from 1 to 4 carbon atoms, and $R_{14}$ represents an alkyl group having from 1 to 4 carbon atoms, in which reaction, while splitting off $R_{14}SH$, there is produced a product of the general formula

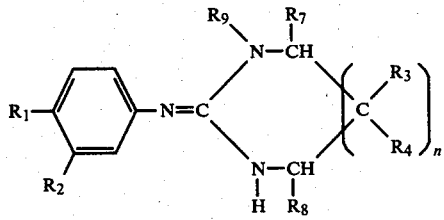

which, if desired, when $R_9$ represents a hydrogen atom, may be converted in the above-described manner into a product of the general formula

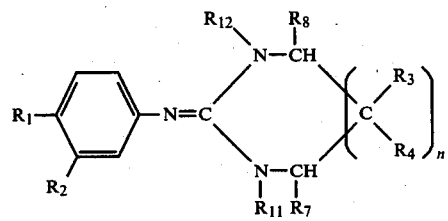

wherein $R_{11}$ and $R_{12}$ are alkanoyl groups having from 2 to 5 carbon atoms.

This reaction is also carried out with the reaction conditions indicated in the second mode of preparation.

The new salts or complexes according to the invention may be prepared by reacting a compound of the general formula

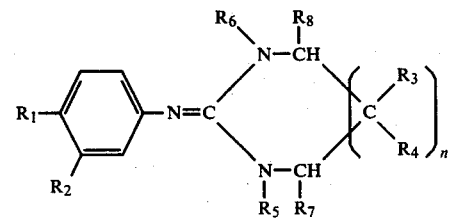

wherein the symbols have the above-indicated meanings and which compound is prepared according to any of the above-indicated methods, with an acid or a salt to be complexed.

Suitable acids are inorganic acids, such as sulphuric acid, phosphoric acid or phosphorous acid, or nitric acid, or organic acids, such as carboxylic acids, phosphonic acids or sulphonic acids. Suitable salts are salts of metals such as zinc, copper, nickel or cobalt.

The conversion into a salt is carried out at room temperature in water, or in a polar organic solvent such as methylene chloride or acetonitrile. The complexing is carried out in a polar organic solvent such as acetonitrile, also at room temperature or a slightly elevated temperature.

Embodiments of the invention will now be described by way of example with reference to the following specific examples.

EXAMPLE 1

Preparation of 2-(4-n-butylphenyl)imino-hexahydropyrimidine

A solution of 144 g. of 4-n-butylphenylisothiocyanate in 800 ml of acetonitrile is added dropwise in 30 minutes at room temperature to a solution of 95 ml of 1,3-diaminopropane in 450 ml of acetonitrile, while solution is stirred. After 1 hour, 260 ml of triethylamine are added. A solution of 212 g of mercurychloride in 560 ml of acetonitrile is then added while stirring said solution for 1 hour. The reaction mixture is stirred for another 24 hours and then filtered while warm. The solvent is distilled from the filtrate and the residue is mixed with up in methylene chloride and washed with dilute alkaline solution and water. After drying, the methylene chloride is distilled off, the crude 2-(4-n-butylphenyl)iminohexahydropyrimidine being obtained in a yield of 165 g. The product can be purified by a recrystallisation from a mixture of carbon tetrachloride and petroleum ether. A product is obtained with a melting point of 116°–119° C. The product may also be purified by dissolving it in approximately 20% hydrochloric acid, washing the aqueous phase with ether and then making it alkaline again. The thus purified 2-(4-n-butylphenyl)imino-hexahydropyrimidine can be isolated by taking up in ether, drying and distilling the solvent. The thus purified product also has a melting point of 116°–119° C.

The following compounds were prepared in a corresponding manner:

2-(4-cyclohexylphenyl)imino-hexahydropyrimidine, melting point 172°–174° C., 2-(4-n-hexylthiophenyl)imino-hexahydropyrimidine, melting point 86° C., 2-(4-isobutylphenyl)imino-hexahydropyrimidine, melting point 99° C., 2-(3,4-tetramethylenephenyl)imino-hexahydropyrimidine, melting point 155° C., 2-(4-n-pentylphenyl)imino-hexahydropyrimidine, melting point 110°–110.5° C., 2-(4-sec.pentylphenyl)imino-hexahydropyrimidine, melting point 124° C., 2-(4-n-hexylphenyl)imino-hexahydropyrimidine, melting point 104° C., 2-(4-n-heptylphenyl)imino-hexahydropyrimidine, melting point 100°–101° C., 2-(4-n-octylphenyl)imino-hexahydropyrimidine, melting point 101°–103° C., 2-(4-n-nonylphenyl)imino-hexahydropyrimidine, melting point 104.5°–105° C., 2-(4-n-decylphenyl)imino-hexahydropyrimidine, melting point 97° C., 2-(4-n-dodecylphenyl)imino-hexahydropyrimidine, melting point 104°–105° C., 2-(4-benzylphenyl)imino-hexahydropyrimidine, melting point 154° C., 2-[4-(2-phenylethyl)phenyl]imino-hexahydropyrimidine, melting point 146° C., 2-(4-n-butylthiophenyl)imino-hexahydropyrimidine, melting point 92° C., 2-(3-n-hexylthiophenyl)imino-hexahydropyrimidine, liquid $n_D^{30} = 1.588$, 2-(4-n-octylthiophenyl)imino-hexahydropyrimidine, melting point 92.5°–94.5° C., 2-[4-(4-methylphenylthio)phenyl]imino-hexahydropyrimidine, melting point 126°–128.5° C., 2-[4-(4-chlorophenylthio)phenyl]imino-hexahydropyrimidine, melting point 148° C.,
2-(4-n-hexyloxyphenyl)imino-hexahydropyrimidine, melting point 117° C.,
2-(4-octyloxyphenyl)imino-hexahydropyrimidine, melting point 113° C.,
2-(4-n-dodecyloxyphenyl)imino-hexahydropyrimidine, melting point 111°–112.5° C.,
2-(4-n-hexyloxycarbonylphenyl)imino-hexahydropyrimidine, melting point 108°–110° C.,
2-(4-n-octyloxycarbonylphenyl)imino-hexahydropyrimidine melting point 100°–101.5° C.,
2-(4-N,N-dibutylaminophenyl)imino-hexahydropyrimidine, viscous liquid,
2-($\beta$-naphthyl)imino-hexahydropyrimidine, melting point 150° C.,
1-methyl-2-(4-n-butylphenyl)imino-hexahydropyrimidine, liquid $n_D^{30}=1.567$,
1-methyl-2-(4-n-hexylphenyl)imino-hexahydropyrimidine, liquid $n_D^{30}=1.554$,
1-methyl-2-(4-cyclohexylphenyl)imino-hexahydropyrimidine, liquid,
2-(4-cyclohexylphenyl)imino-5,5-dimethylhexahydropyrimidine, melting point 160° C. (decomposition),
2-(4-n-butylphenyl)imino-imidazolidine, melting point 85° C.,
2-(4-cyclohexylphenyl)imino-imidazolidine, melting point 163°–165° C. (decomposition),
2-(4n-hexylphenyl)imino-imidazolidine, melting point 98° C.,
2-(4-n-heptylphenyl)imino-imidazolidine, melting point 88°–90° C.,
2-(4-n-octylphenyl)imino-imidazolidine, melting point 80°–82° C.,
2-(4-n-butylthiophenyl)imino-imidazolidine, melting point 96° C.,
2-(4-n-hexylthiophenyl)imino-imidazolidine, melting point 57° C.,
2-(4-n-octylthiophenyl)imino-imidazolidine, melting point 69°–71° C.,
2-[4-(4-methylphenylthio)phenyl]imino-imidazolidine, melting point 113° C.,
2-[4-(4-chlorophenylthio)phenyl]imino-imidazolidine, melting point 152° C.,
2-(4-sec.octyloxycarbonylphenyl)imino-imidazolidine, melting point 78°–83° C.,
2-[4-(4-chlorophenylthio)phenyl]imino-imidazolidine, melting point 125° C.,
2-[4-{2-(4-methylphenyl)ethyl}phenyl]imino-hexahydropyrimidine, melting point 161° C.,
2-(4-cyclohexylphenyl)imino-4-methyl-hexahydropyrimidine, melting point 146° C.,
2-(4-n-butylphenyl)imino-4-methyl-hexahydropyrimidine, oil,
2-(4-n-octylphenyl)imino-4-methyl-hexahydropyrimidine, melting point 78° C.,
2-[4-{2-(2-methylphenyl)ethyl}phenyl]imino-hexahydropyrimidine, oil,
2-[4-{2-(4-isopropylphenyl)ethyl}phenyl]imino-hexahydropyrimidine, melting point 154° C.,
2-[4-{2-(4-ethoxyphenyl)ethyl}phenyl]imino-hexahydropyrimidine, melting point 142° C.,
2-[4-{2-(4-isopropoxyphenyl)ethyl}phenyl]imino-hexahydropyrimidine, melting point 158° C.,
2-[4-{2-(4-chlorophenyl)ethyl}phenyl]imino-hexahydropyrimidine, melting point 149° C.,
2-[4-{2-(2-chlorophenyl)ethyl}phenyl]imino-hexahydropyrimidine, melting point 153° C.,
2-[4-{2-(3,4-dichlorophenyl)ethyl}phenyl]imino-hexahydropyrimidine, melting point 124° C.,
2-[4-(2-furylethyl)phenyl]imino-hexahydropyrimidine, melting point 135° C.,
2-(4-isopentylthiophenyl)imino-hexahydropyrimidine,
2-[4-{2-(4-n-butoxyphenyl)ethyl}phenyl]imino-hexahydropyrimidine,
2-[4-{2-(4-benzylphenyl)ethyl}phenyl]imino-hexahydropyrimidine.

EXAMPLE 2

Preparation of 2-(4-cyclohexylphenyl)imino-hexahydropyrimidine

A solution of 2.9 g of N-(3-aminopropyl)-N'-(4-cyclohexylphenyl)thiourea and 0.65 ml of methyliodide in 20 ml of amyl alcohol is slowly heated to the boiling point and then refluxed for 1 hour. After distilling off the solvent, the residue is taken up in methylene chloride and washed with dilute alkaline solution and water. The methylene chloride is distilled off and the crude 2-(4-cyclohexylphenyl)imino-hexahydropyrimidine is recrystallised from acetonitrile. The purified product has a melting point of 179°–181° C.

EXAMPLE 3

Preparation of 2-(4-cyclohexylphenyl)imino-hexahydropyrimidine

A solution of 3.6 g of N-(4-cyclohexylphenyl)-S-methyl-isothiourea hydroiodide and 1 ml of 1,3-diaminopropane in 15 ml of amyl alcohol is refluxed for $2\frac{1}{2}$ hours. After distilling off the solvent the residue is taken up in methylene chloride and washed with dilute alkaline solution and water. The methylene chloride is distilled off and the crude final product is recrystallised from acetonitrile. The resulting 2-(4-cyclohexylphenyl)imino-hexahydropyrimidine has a melting point of 179°–181° C.

EXAMPLE 4

Preparation of 2-(4-cyclohexylphenyl)imino-hexahydropyrimidine

A solution of 2.6 g of N-dichloromethylene 4-cyclohexylaniline in 40 ml of acetonitrile is added dropwise to a solution of 1 ml of 1,3-diaminopropane in 20 ml of acetonitrile in 15 minutes at room temperature. After the addition of 1 ml of triethylamine, the solution is stirred for 1 hour at room temperature, after which the reaction mixture is filtered while warm. After distilling off the solvent the residue is taken up in ether and successively washed with 2 N sodium hydroxide solution and water. The ether layer is dried and evaporated, after which the residue is recrystallised from acetonitrile. The resulting 2-(4-cyclohexylphenyl)imino-hexahydropyrimidine has a melting point of 180°–182° C.

2-(4-n-hexylphenyl)imino-hexahydropyrimidine was prepared in a corresponding manner.

EXAMPLE 5

Preparation of 2-(4-cyclohexylphenyl)imino-hexahydropyrimidine

A solution of 5.9 g of N-[bis-(,ethylthio)methylidene]-p-cyclohexylaniline and 2.1 ml of 1,3-diaminopropane in 30 ml of amyl alcohol is refluxed for $2\frac{1}{2}$ hours. After distilling off the solvent, the residue is taken up in methylene chloride and successively washed with dilute sodium hydroxide solution and water. The methylene chloride is distilled off and the crude final product is recrystallised from acetonitrile. The resulting 2-(4-cyclohexylphenyl)imino-hexahydropyrimidine has a melting point of 178°–180° C.

EXAMPLE 6

Preparation of 2-(4-cyclohexylphenyl)imino-imidazolidine 9.1 g of p-cyclohexylaniline and 11.9 g of 2-n-butyl-thioimidazolidine hydrobromide in 60 ml of amyl alcohol are refluxed for 6 hours. The solvent is then distilled off in vacuo. The residue is taken up in methylene chloride and successively washed with dilute sodium hydroxide solution and water. The methylene chloride is distilled off and the crude final product is recrystallised from acetonitrile. The resylting 2-(4-cyclohexylphenyl)imino-imidazolidine decomposes at 163° C.

EXAMPLE 7

Preparation of 2-(4-cyclohexylphenyl)imino-hexahydropyrimidine sulphate 36 g of 2-(4-cyclohexylphenyl)imino-hexahydropyrimidine are dissolved in 140 ml of 1 N sulphuric acid. After evaporation in vacuo the 2-(4-cyclohexylphenyl)imino-hexahydropyrimidine sulphate is obtained; melting point approximately 260° C.

The following salts are prepared in a corresponding manner, on the understanding that starting from organic acids use is made of organic solvents, such as methylene chloride and acetonitrile:

2-(4-cyclohexylphenyl)imino-hexahydropyrimidine cinnamate,
2-(4-cyclohexylphenyl)imino-hexahydropyrimidine β-chloroethane phosphonate; melting point approximately 190° C.,
2-(4-cyclohexylphenyl)imino-hexahydropyrimidine p-dodecylbenzene sulphonate,
2-(4-cyclohexylphenyl)imino-hexahydropyrimidine acetate, melting point approximately 170° C.,
2-(4-n-octylphenyl)imino-hexahydropyrimidine acetate, melting point approximately 75° C.,
2-(4-cyclohexylphenyl)imino-hexahydropyrimidine-phosphorous acid ethyl ester,
2-(4-cyclohexylphenyl)imino-hexahydroyrimidine phosphorous acid-n-butyl ester.

EXAMPLE 8

Preparation of 2-(4-cyclohexylphenyl)imino-hexahydropyrimdine zinc chloride complex 10.3 g of 2-(4-cyclohexylphenyl)imino-hexahydropyrimidine are dissolved in 150 ml of warm acetonitrile. To this solution is added a warm solution of 2.7 g of zinc-chloride in acetonitrile. The solvent is then evaporated after which the 2-(4-cyclohexylphenyl)imino-hexahydropyrimidine zinc chloride complex is obtained. The complex is characterized by the I.R.-spectrum.

In a corresponding manner the following complexes are prepared:

2-(4-cyclohexylphenyl)imino-hexahydropyrimidine zinc acetate complex,
2-(4-cyclohexylphenyl)imino-hexahydropyrimidine cupric acetate complex,
2-(4-n-octylphenyl)imino-hexahydropyrimidine zinc chloride complex,
2-(4-n-butylphenyl)imino-hexahydropyrimidine cupric acetate complex.

EXAMPLE 9

Preparation of 1,3-diacetyl-2-(4-cyclohexylphenyl)imino-hexahydropyrimidine 2.8 g of 2-(4-cyclohexylphenyl)imino-hexahydropyrimidine and 50 ml of acetic acid anhydride are refluxed for 2 hours. After distilling off the volatile constituents under reduced pressure the residue is recrystallised from acetonitrile. The resulting 1,3-diacetyl-2-(4-cyclohexylphenyl)imino-hexahydropyrimidine melts at 154.5°–155.5° C.

EXAMPLE 10

The compounds according to the invention are processed into compositions by suspensing the compounds in water in the presence of a dispersing agent, such as lignin sulphonate, and/or a wetting agent, such as naphthalene sulphonate, an alkyl sulphate, an alkyl benzene sulphonate, a quaternary ammonium chloride, an alkylpolyoxyethylene or an alkylarylpolyoxyethylene. In a few cases the compounds are dissolved in water, if desired by means of a water-miscible organic solvent and if desired in the presence of an emulsifier, for example with polyoxyethylene groups modified ricinic oil or an alkylarylpolyoxyethylene.

The crop to be protected against bean rust (*Uromyces phaseoli*) is then treated with the composition as described in the preamble.

The results of the treatment are recorded in the table below. The table gives the minimum concentration of the compound used (in ppm) at which an effective protection of the relevant crop, in this case dwarf French beans, against *Uromyces phaseoli* was still found.

| Compound | min. concentration in ppm |
| --- | --- |
| 2-(4-n-butylphenyl)imino-hexahydropyrimidine | 10 |
| 2-(4-n-hexylphenyl)imino-hexahydropyrimidine | <10 |
| 2-(4-cyclohexylphenyl)imino-hexahydropyrimidine | <10 |
| 2-(4-n-octylphenyl)imino-hexahydropyrimidine | <10 |
| 2-(4-n-butylthiophenyl)imino-hexahydropyrimidine | <10 |
| 2-(3-n-hexylthiophenyl)imino-hexahydropyrimidine | 10–30 |
| 2-(4-n-hexylthiophenyl)imino-hexahydropyrimidine | 10 |
| 2-[4-(4-methylphenylthio)phenyl]imino-hexahydropyrimidine | <10 |
| 2-[4-(4-chlorophenylthio)phenyl]imino-hexahydropyrimidine | <10 |
| 2-(4-n-hexyloxycarbonylphenyl)imino-hexahydropyrimidine | <10 |
| 2-(4-n-octyloxycarbonylphenyl)imino-hexahydropyrimidine | <10 |
| 2-(4-n-octylphenyl)imino-imidazolidine | <10 |
| 2-(4-cyclohexylphenyl)imino-imidazolidine | <10 |
| 2-(4-n-hexylthiophenyl)imino-imidazolidine | 10 |
| 2-(4-n-butylthiophenyl)imino-imidazolidine | 10 |

-continued

| Compound | min. concentration in ppm |
|---|---|
| 2-[4-(4-methylphenylthio)phenyl]imino-imidazolidine | 10 |
| 2-[4-(4-chlorophenylthio)phenyl]imino-imidazolidine | <10 |
| 1,3-diacetyl-2-(4-cyclohexylphenyl)-imino-hexahydropyrimidine | <10 |
| 2-(4-n-pentylphenyl)imino-hexahydropyrimidine | <10 |
| 2-(4-n-heptylphenyl)imino-hexahydropyrimidine | 10 |
| 2-(4-benzylphenyl)imino-hexahydropyrimidine | 10–30 |
| 2-[4-(2-phenylethyl)phenyl]imino-hexahydropyrimidine | 10–30 |
| 2-(4-n-hexylphenyl)imino-1-methyl-hexahydropyrimidine | 10–30 |
| 2-(4-n-butylphenyl)imino-imidazolidine | 10–30 |
| 2-(4-n-hexylphenyl)imino-imidazolidine | <10 |
| 2-(4-n-heptylphenyl)imino-imidazolidine | 10–30 |
| 2-(4-n-octylthiophenyl)imino-imidazolidine | 10 |
| 2-(4-sec.octyloxycarbonylphenyl)imino-imidazolidine | 10–30 |
| 2-[4-(4-chlorophenylthio)phenyl]imino-4-methyl-imidazolidine | 10–30 |
| 2-(4-cyclohexylphenyl)imino-hexahydropyrimidine sulphate | <10 |
| 2-(4-cyclohexylphenyl)imino-hexahydropyrimidine cinnamate | 10 |
| 2-(4-cyclohexylphenyl)imino-hexahydropyrimidine β-chloroethanephosphonate | <10 |
| 2-(4-cyclohexylphenyl)imino-hexahydropyrimidine p-dodecylbenzene sulphonate | 10 |
| 2-(4-cyclohexylphenyl)imino-hexahydropyrimidine acetate | <10 |

EXAMPLE 11

The crop to be protected against brown wheat rust (*Puccinia recondita*) is treated as described in the preamble with a composition obtained as indicated in Example 10.

The results of the treatment are recorded in the table below. Said table indicates the minimum concentration of the compound used at which an effective protection of the relevant crop, in this case wheat, against *Puccinia recondita* was still found.

| Compound | min. concentration in ppm |
|---|---|
| 2-(4-n-butylphenyl)imino-hexahydropyrimidine | 300 |
| 2-(4-n-hexylphenyl)imino-hexahydropyrimidine | ≧300 |
| 2-(4-cyclohexylphenyl)imino-hexahydropyrimidine | 100–300 |
| 2-(4-n-octylphenyl)imino-hexahydropyrimidine | 100–300 |
| 2-(4-n-decylphenyl)imino-hexahydroxypyrimidine | ≧300 |
| 2-(4-n-hexylthiophenyl)imino-hexahydropyrimidine | 300 |
| 2-(4-n-hexyloxycarbonylphenyl)imino-hexahydropyrimidine | 300 |
| 2-(4-cyclohexylphenyl)imino-5,5-dimethyl-hexahydropyrimidine | 300 |
| 2-(4-n-heptylphenyl)imino-hexahydropyrimidine | 300 |
| 2-(4-n-nonylphenyl)imino-hexahydropyrimidine | 300 |

-continued

| Compound | min. concentration in ppm |
|---|---|
| 2-[4-(-2-phenylethyl)phenyl]imino-hexahydropyrimidine | 100–300 |
| 2-(4-cyclohexylphenyl)imino-hexahydropyrimidine sulphate | 100–300 |
| 2-(4-cyclohexphenyl)imino-hexahydropyrimidine cinnamate | 100–300 |
| 2-(4-cyclohexylphenyl)imino-hexahydropyrimidine β-chloroethanephosphonate | 100–300 |
| 2-(4-cyclohexylphenyl)imino-hexahydropyrimidine p-dodecylbenzene sulphonate | 100–300 |
| 2-(4-cyclohexylphenyl)imino-hexahydropyrimidine acetate | 100 |
| 2-[4-{2-(4-methylphenyl)ethyl}phenyl]imino-hexahydropyrimidine | 100–300 |
| 2-(4-cyclohexylphenyl)imino-4-methyl-hexahydropyrimidine | 100–300 |
| 2-(4-n-butylphenyl)imino-4-methyl-hexahydropyrimidine | 300 |
| 2-(4-n-octylphenyl)imino-4-methyl hexahydropyrimidine | 300 |
| 2-[4-{2-(4-chlorophenyl)ethyl}phenyl]imino-hexahydropyrimidine | 100 |

EXAMPLE 12

The crop to be protected against mildew on cereals (*Erysiphe graminis*) is treated as described in the preamble with a composition obtained as described in Example 10.

The results of the treatment are recorded in the table below. Said table indicates the minimum concentration of the compound used at which an effective protection of the relevant crop, in this case barley, against *Erysiphe graminis* was still found.

| Compound | min. concentration in ppm |
|---|---|
| 2-(4-n-butylphenyl)imino-hexahydropyrimidine | 100 |
| 2-(4-isobutylphenyl)imino-hexahydropyrimidine | 100 |
| 2-(4-n-hexylphenyl)imino-hexahydropyrimidine | 100–300 |
| 2-(4-cyclohexylphenyl)imino-hexahydropyrimidine | 100 |
| 2-(4-n-butylthiophenyl)imino-hexahydropyrimidine | 100 |
| 2-(4-n-hexylthiophenyl)imino-hexahydropyrimidine | 300 |
| 1-methyl-2-(4-cyclohexylphenyl)imino-hexahydropyrimidine | 100 |
| 2-(4-cyclohexylphenyl)imino-5,5-dimethyl-hexahydropyrimidine | 100 |
| 2-(β-naphthyl)imino-hexahydropyrimidine | 100 |
| 2-(3,4-tetramethylenephenyl)imino-hexahydropyrimidine | 300 |
| 2-(4-n-heptylphenyl)imino-hexahydropyrimidine | 300 |
| 2-(4-n-nonylphenyl)imino-hexahydropyrimidine | 100 |
| 2-(4-n-dodecylphenyl)imino-hexahydropyrimidine | 300 |
| 2-(4-isopentylthiophenyl)imino-hexahydropyrimidine | 100–300 |
| 2-[4-{2-(4-methylphenyl)ethyl}phenyl]imino-hexahydropyrimidine | 100 |
| 2-[4-{2-(4-chlorophenyl)ethyl}phenyl]imino-hexahydropyrimidine | 100 |
| 2-[4-{2-(4-isopropoxyphenyl)ethyl}phenyl]imino-hexahydropyrimidine | 100 |

| Compound | min. concentration in ppm |
|---|---|
| 2-[4-{2-(2-methylphenyl)ethyl}phenyl]imino-hexahydropyrimidine | 100 |
| 2-[4-(2-furylethyl)phenyl]imino-hexahydropyrimidine | 100 |
| 2-[4-{2-(4-isopropylphenyl)ethyl}phenyl]imino-hexahydropyrimidine | 100 |
| 2-[4-{2(4-ethoxyphenyl)ethyl}phenyl]imino-hexahydropyrimidine | 100 |
| 2-[4-{2-(4-n-butoxyphenyl)ethyl}phenyl]imino-hexahydropyrimidine | 300 |
| 2-(4-benzylphenyl)imino-hexahydropyrimidine | 300 |
| 2-[4-(2-phenylethyl)phenyl]imino-hexahydropyrimidine | 300 |
| 2-(4-n-butylphenyl)imino-1-methyl-hexahydropyrimidine | 100–300 |
| 2-(4-N,N—dibutylaminophenyl)imino-hexahydropyrimidine | 100–300 |
| 2-(4-cyclohexylphenyl)imino-4-methyl hexahydropyrimidine | 100–300 |
| 2-(4-cyclohexylphenyl)imino-hexahydropyrimidine sulphate | 100–300 |
| 2-(4-cyclohexylphenyl)imino-hexahydropyrimidine cinnamate | 100–300 |
| 2-(4-cyclohexylphenyl)imino-hexahydropyrimidine β-chloroethanephosphonate | 100–300 |
| 2-(4-cyclohexylphenyl)imino-hexahydropyrimidine p-dodecylbenzene sulphonate | 100–300 |
| 2-(4-cyclohexylphenyl)imino-hexahydropyrimidine acetate | 100–300 |
| 2-(4-cyclohexylphenyl)imino-hexahydropyrimidine zinc chloride complex | 100–300 |
| 2-(4-cyclohexylphenyl)imino-hexahydropyrimidine zinc acetate complex | 100–300 |
| 2-(4-n-octylphenyl)imino-hexahydropyrimidine acetate | 300 |
| 2-(4-n-octylphenyl)imino-hexahydropyrimidine zinc chloride complex | 300 |

EXAMPLE 13

The crop to be protected against mildew on apple (*Podosphaera leucotricha*) is treated with a composition obtained as indicated in Example 10. The treatment is carried out by spraying young apple seedlings, approximately 15 cm high, with an aqueous suspension or solution of the compound to be tested in different concentrations. After drying up of the liquid, the seedlings are infected with spores of *Podosphaera leucotricha*. After an incubation period of 14 days at a temperature of 18° C. and a relative humidity of approximately 80% it is tested to what extent, if any, the mould has developed. The results are recorded in the table below. Said table indicates the minimum concentration of the compound used at which an effective protection of the relevant crop, in this case apple seedlings, against *Podosphaera leucotricha* was still found.

| Compound | min. concentration in ppm |
|---|---|
| 2-(4-n-octylphenyl)imino-hexahydropyrimidine | 100–300 |
| 2-(4-benzylphenyl)imino-hexahydropyrimidine | 100 |
| 2-[4-(2-phenylethyl)phenyl]imino-hexahydropyrimidine | 100 |
| 2-(4-octylthiophenyl)imino-hexahydropyrimidine | 100–300 |

What is claimed is:

1. A compound of the formula:

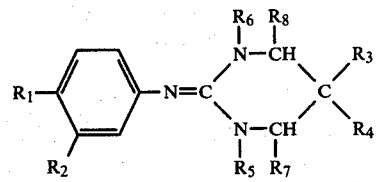

wherein $R_1$ or $R_2$ equal or different and represent any of a hydrogen atom, a $C_4$–$C_{12}$ alkyl group, a $C_4$–$C_{12}$ alkyloxy group, a $C_4$–$C_{12}$ alkylthio group, a $C_3$–$C_7$ cycloalkyl group, a benzyloxy group, a benzylthio group, a phenoxy group, a phenylthio group, a benzyloxy group substituted with halogen or $C_1$–$C_4$ alkyl, a benzylthio group substituted with halogen or $C_1$–$C_4$ alkyl, a phenoxy group substituted with halogen or $C_1$–$C_4$ alkyl, a phenylthio group substituted with halogen or $C_1$–$C_4$ alkyl, a $C_7$–$C_{11}$ phenylalkyl group, a $C_7$–$C_{11}$ phenylalkyl group substituted with halogen, benzyl, di($C_1$–$C_6$ alkyl)amino, $C_1$–$C_6$ alkyl, $C_1$–$C_6$ alkoxy, $C_1$–$C_6$ alkylthio, halo $C_1$–$C_6$ alkyl, halo $C_1$–$C_6$ alkoxy, or halo $C_1$–$C_6$ alkylthio; furyl $C_1$–$C_4$ alkyl, thienyl $C_1$–$C_4$ alkyl, di($C_2$–$C_6$ alkyl)amino, or $C_4$–$C_{12}$ alkoxycarbonyl, or wherein $R_1$ and $R_2$ together represent a trimethylene or tetramethylene group with the proviso that $R_1$ and $R_2$ are not both hydrogen atoms, $R_3$, $R_4$, $R_7$, and $R_8$ are equal or different and represent any of a hydrogen atom or $C_1$–$C_4$ alkyl, and $R_5$ and $R_6$ are equal or different and represent any of a hydrogen atom, $C_1$–$C_4$ alkyl, or $C_2$–$C_5$ alkanoyl, and salts or complexes thereof.

2. The compound of claim 1 which is 2-[4-{2-(4-benzylphenyl)ethyl}phenyl]imino-hexahydropyrimidine.

3. A compound of the formula:

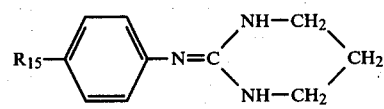

wherein $R_{15}$ is a $C_4$–$C_{12}$ alkyl group, a $C_4$–$C_{12}$ alkylthio group, cyclohexyl, phenylthio, a phenylthio group substituted with halogen or $C_1$–$C_4$ alkyl, $C_7$–$C_{11}$ phenylalkyl, a $C_7$–$C_{11}$ phenylalkyl group wherein the phenyl group is substituted with halogen, $C_1$–$C_6$ alkyl, or $C_1$–$C_6$ alkoxy; furyl $C_1$–$C_4$ alkyl, or $C_4$–$C_{12}$ alkoxycarbonyl, and salts and complexes thereof.

4. 2-(4-cyclohexylphenyl)imino-hexahydropyrimidine.

5. 2-(4-n-octylphenyl)imino-hexahydropyrimidine.

6. 2-(4-n-butylphenyl)imine-hexahydropyrimidine.

7. 2-(4-n-hexylphenyl)imino-hexahydropyrimidine.

8. 2-(4-n-butylthiophenyl)imino-hexahydropyrimidine.

9. 2-(4-n-hexylthiophenyl)imino-hexahydropyrimidine.

10. 2-[4-(4-methylphenylthio)phenyl]imino-hexahydropyrimidine.

11. 2-[4-(4-chlorophenylthio)phenyl]imino-hexahydropyrimidine.

12. 2-(4-n-hexyloxycarbonylphenyl)imino-hexahydropyrimidine.

13. 2-(4-n-octyloxycarbonylphenyl)imino-hexahydropyrimidine.
14. 2-(4-n-heptylphenyl)imino-hexahydropyrimidine.
15. 2-(4-n-nonylphenyl)imino-hexahydropyrimidine.
16. 2-[4-(2-phenylethyl)phenyl]imino-hexahydropyrimidine.
17. 2-[4-{2-(4-chlorophenyl)ethyl}phenyl]iminohexahydropyrimidine.
18. 2-[4-{2-(4-methylphenyl)ethyl}phenyl]iminohexahydropyrimidine.
19. 2-[4-{2-(4-isopropylphenyl)ethyl}phenyl]iminohexahydropyrimidine.
20. 2-[4-(2-furylethyl)phenyl]imino-hexahydropyrimidine.
21. 2-(4-cyclohexylphenyl)imino-hexahydropyrimidine sulphate.
22. 2-(4-cyclohexylphenyl)imino-hexahydropyrimidine cinnamate.
23. 2-(4-cyclohexylphenyl)imino-hexahydropyrimidine$\beta$-chloroethanephosphonate.
24. 2-(4-cyclohexylphenyl)imino-hexahydropyrimidine p-dodecylbenzene sulphonate.
25. 2-(4-cyclohexylphenyl)imino-hexahydropyrimidine acetate.
26. 2-(4-cyclohexylphenyl)imino-hexahydropyrimidine zinc chloride complex.
27. 2-(4-cyclohexylphenyl)imino-hexahydropyrimidine zinc acetate complex.
28. A fungicidal composition comprising a fungicidally effective amount of a compound of the formula:

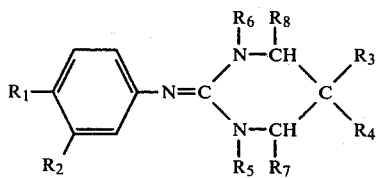

wherein $R_1$ or $R_2$ are equal or different and represent any of a hydrogen atom, a $C_4$–$C_{12}$ alkyl group, a $C_4$–$C_{12}$ alkyloxy group, a $C_4$–$C_{12}$ alkylthio group, a $C_3$–$C_7$ cycloalkyl group, a benzyloxy group, a benzylthio group, a phenoxy group, a phenylthio group, a benzyloxy group substituted with halogen or $C_1$–$C_4$ alkyl, a benzylthio group substituted with halogen or $C_1$–$C_4$ alkyl, a phenoxy group substituted with halogen or $C_1$–$C_4$ alkyl, a phenylthio group substituted with halogen or $C_1$–$C_4$ alkyl, a $C_7$–$C_{11}$ phenylalkyl group, a $C_7$–$C_{11}$ phenylalkyl group substituted with halogen, benzyl, di($C_1$–$C_6$ alkyl)amino, $C_1$–$C_6$ alkyl, $C_1$–$C_6$ alkoxy, $C_1$–$C_6$ alkylthio, halo $C_1$–$C_6$ alkyl, halo $C_1$–$C_6$ alkoxy, or halo $C_1$–$C_6$ alkylthio; furyl $C_1$–$C_4$ alkyl, thienyl $C_1$–$C_4$ alkyl, di($C_2$–$C_6$ alkyl)amino, or $C_4$–$C_{12}$ alkoxycarbonyl, or wherein $R_1$ and $R_2$ together represent a trimethylene or tetramethylene group with the proviso that $R_1$ and $R_2$ are not both hydrogen atoms, $R_3$, $R_4$, $R_7$, and $R_8$ are equal or different and represent any of a hydrogen atom or $C_1$–$C_4$ alkyl, and $R_5$ and $R_6$ are equal or different and represent any of a hydrogen atom, $C_1$–$C_4$ alkyl, or $C_2$–$C_5$ alkanoyl, and salts or complexes thereof and an inert finely divided carrier therefor.

29. The fungicidal composition of claim 28 wherein said compound is 2-[4-{2-(4-benzylphenyl)ethyl}-phenyl]imino-hexahydropyrimidine.
30. A composition as claimed in claim 28, characterized in that the active constituent is 2-(4-cyclohexylphenyl)imino-hexahydropyrimidine.
31. A composition as claimed in claim 28, characterized in that the active constituent is 2-(4-n-octylphenyl)imino-hexahydropyrimidine.
32. A composition as claimed in claim 28, characterized in that the active constituent is 2-(4-n-butylphenyl)imino-hexahydropyrimidine.
33. A composition as claimed in claim 28, characterized in that the active constituent is 2-(4-n-hexylphenyl)imino-hexahydropyrimidine.
34. A composition as claimed in claim 28, characterized in that the active constituent is 2-(4-n-butylthiophenyl)imino-hexahydropyrimidine.
35. A composition as claimed in claim 28, characterized in that the active constituent is 2-(4-n-hexylthiophenyl)imino-hexahydropyrimidine.
36. A composition as claimed in claim 28, characterized in that the active constituent is 2-[4-(4-methylphenylthio)phenyl]imino-hexahydropyrimidine.
37. A composition as claimed in claim 28, characterized in that the active constituent is 2-[4-(4-chlorophenylthio)phenyl]imino-hexahydropyrimidine.
38. A composition as claimed in claim 28, characterized in that the active constituent is 2-(4-n-hexyloxycarbonylphenyl)imino-hexahydropyrimidine.
39. A composition as claimed in claim 28, characterized in that the active constituent is 2-(4-n-octyloxycarbonylphenyl)imino-hexahydropyrimidine.
40. A composition as claimed in claim 28, characterized in that the active constituent is 2-(4-n-heptylphenyl)imino-hexahydropyrimidine.
41. A composition as claimed in claim 28, characterized in that the active constituent is 2-(4-n-nonylphenyl)imino-hexahydropyrimidine.
42. A composition as claimed in claim 28, characterized in that the active constituent is 2-[4-(2-phenylethyl)phenyl]imino-hexahydropyrimidine.
43. A composition as claimed in claim 28, characterized in that the active constituent is 2-[4-{2-(4-chlorophenyl)ethyl}phenyl]imino-hexahydropyrimidine.
44. A composition as claimed in claim 28, characterized in that the active constituent is 2-[4-{2-(4-methylphenyl)ethyl}phenyl]imino-hexahydropyrimidine.
45. A composition as claimed in claim 28, characterized in that the active constituent is 2-[4-{2-(4-isopropylphenyl)ethyl}phenyl]imino-hexahydropyrimidine.
46. A composition as claimed in claim 28, characterized in that the active constituent is 2-[4-(2-furylethyl)-phenyl]imino-hexahydropyrimidine.
47. A composition as claimed in claim 28, characterized in that the active constituent is 2-(4-cyclohexylphenyl)imino-hexahydropyrimidine sulphate.
48. A composition as claimed in claim 28, characterized in that the active constituent is 2-(4-cyclohexylphenyl)imino-hexahydropyrimidine cinnamate.
49. A composition as claimed in claim 28, characterized in that the active constituent is 2-(4-cyclohexylphenyl)imino-hexahydropyrimidine$\beta$-chloroethane phosphate.
50. A composition as claimed in claim 28, characterized in that the active constituent is 2-(4-cyclohexylphenyl)imino-hexahydropyrimidine p-dodecylbenzene sulphonate.

51. A composition as claimed in claim 28, characterized in that the active constituent is 2-(4-cyclohexylphenyl)imino-hexahydropyrimidine acetate.

52. A composition as claimed in claim 28, characterized in that the active constituent is 2-(4-cyclohexylphenyl)imino-hexahydropyrimidine zinc chloride complex.

53. A composition as claimed in claim 28, characterized in that the active constituent is 2-(4-cyclohexylphenyl)imino-hexahydropyrimidine zinc acetate complex.

54. A fungicidal composition comprising a fungicidally effective amount of a compound of the formula:

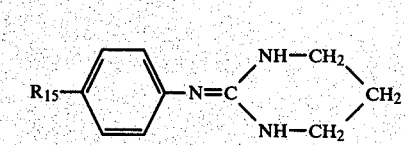

wherein $R_{15}$ is a $C_4$-$C_{12}$ alkyl group, a $C_4$-$C_{12}$ alkylthio group, cyclohexyl, phenylthio, a phenylthio group substituted with halogen or $C_1$-$C_4$ alkyl, $C_7$-$C_{11}$ phenylalkyl, a $C_7$-$C_{11}$ phenylalkyl group wherein the phenyl group is substituted with halogen, $C_1$-$C_6$ alkyl, or $C_1$-$C_6$ alkoxy; furyl $C_1$-$C_4$ alkyl, or $C_4$-$C_{12}$ alkoxycarbonyl, and salts and complexes thereof and an inert finely divided carrier therefor.

55. A method of preventing or combating mould infections in agriculture and horticulture, comprising treating the crop to be protected or the infected crop with a composition of claim 28 in a dosage of from 200 g to 1000 g of active substance per ha.

* * * * *

UNITED STATES PATENT AND TRADEMARK OFFICE
CERTIFICATE OF CORRECTION

PATENT NO. : 4,396,617
DATED : August 2, 1983
INVENTOR(S) : Hendrik DOLMAN, Johannes KUIPERS It is certified that error appears in the above-identified patent and that said Letters Patent is hereby corrected as shown below:

In the heading of the patent please correct

"[73] Assignee: Duphar International B.V." to read

--[73] Assignee: Duphar International Research B.V.--.

Signed and Sealed this

Twenty-sixth Day of March 1985

[SEAL]

Attest:

DONALD J. QUIGG

Attesting Officer   Acting Commissioner of Patents and Trademarks